(12) United States Patent
Renna et al.

(10) Patent No.: US 9,062,343 B2
(45) Date of Patent: Jun. 23, 2015

(54) INTEGRATED DEVICE FOR REAL TIME QUANTITATIVE PCR

(71) Applicant: STMicroelectronics S.r.l, Agrate Brianza (IT)

(72) Inventors: Lucio Renna, Acireale (IT); Clelia Carmen Galati, San Gregorio di Catania (IT); Natalia Maria Rita Spinella, Paterno (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 13/856,473

(22) Filed: Apr. 4, 2013

(65) Prior Publication Data

US 2013/0224744 A1 Aug. 29, 2013

(30) Foreign Application Priority Data

Apr. 5, 2012 (IT) ................ TO2012A0302

(51) Int. Cl.
*C12Q 1/68* (2006.01)

(52) U.S. Cl.
CPC ............ *C12Q 1/6816* (2013.01); *C12Q 1/6844* (2013.01); *C12Q 1/6851* (2013.01); *C12Q 2563/107* (2013.01)

(58) Field of Classification Search
CPC ........... C12Q 2563/143; C12Q 1/6844; C12Q 1/6816
USPC .............................. 435/6.11, 287.2
See application file for complete search history.

(56) References Cited

U.S. PATENT DOCUMENTS

| 3,013,467 | A | * | 12/1961 | Minsky ................ 356/432 |
| 5,686,271 | A | * | 11/1997 | Mian et al. ............. 435/91.1 |
| 6,310,354 | B1 | * | 10/2001 | Hanninen et al. ....... 250/458.1 |

| 2006/0029959 | A1 | * | 2/2006 | Okamoto et al. ............ 435/6 |
| 2008/0305481 | A1 | | 12/2008 | Whitman et al. |
| 2012/0248347 | A1 | | 10/2012 | Renna et al. |

FOREIGN PATENT DOCUMENTS

| EP | 2077336 | | 7/2009 | |
| IT | IO 30740 | | 8/2012 | |
| JP | 2000102400 | * | 4/2000 | ............... C12Q 1/68 |
| WO | 2006/131892 | | 12/2006 | |
| WO | 2008/074023 | | 6/2008 | |
| WO | 2009/069009 | | 6/2009 | |
| WO | 2011/020011 | | 2/2011 | |

OTHER PUBLICATIONS

Translation of JP2000-102400 retrieved from JPO on Jun. 1, 2014.*
Dynabead manual 2014, retrieved from www.dynalbiotech.com.*
Lermo et al., "In situ DNA amplification with magnetic primers for the electrochemical detection of food pathogens", Biosensors and Bioelectronics 22(9-10): 2010-2017 (2007).
C.S. Jacobsen, "Microscale detection of specific bacterial DNA in soil with a magnetic capture-hybridization and PCR amplification assay", Appl. Environ. Microbiol. 61(9): 3347-3352 (1995).
Cafer T. Yavuz et al. Low-Field Magnetic Separation of monodisperse nanocrystals, Science 314 (5801): 964-967 (2006).

* cited by examiner

*Primary Examiner* — Angela M Bertagna
*Assistant Examiner* — Olayinka Oyeyemi
(74) *Attorney, Agent, or Firm* — Seed IP Law Group PLLC

(57) ABSTRACT

A method for real-time quantitative detection of single-type, target nucleic acid sequences amplified using a PCR in a microwell, comprising introducing in the microwell a sample comprising target nucleic acid sequences, magnetic primers, and labelling probes; performing an amplification cycle to form labelled amplicons; attracting the magnetic primers to a surface through a magnetic field to form a layer including labelled amplification products and free magnetic primers; and detecting the labelled amplification products in the layer with a surface-specific reading method.

14 Claims, 7 Drawing Sheets

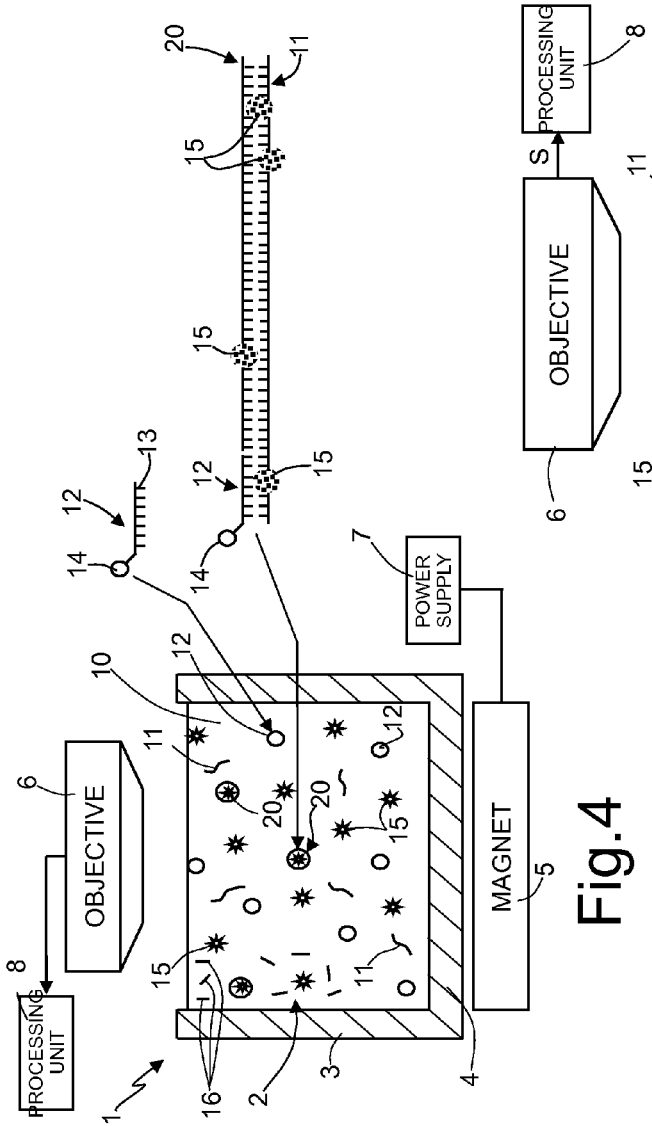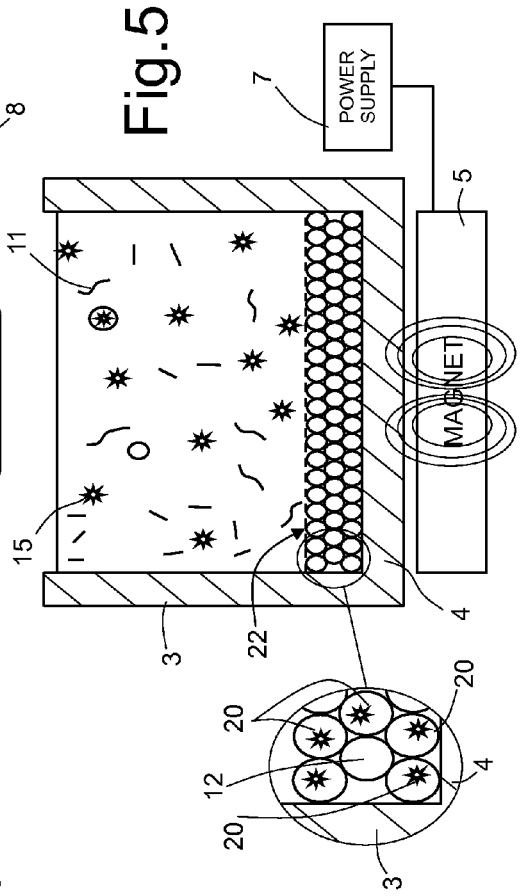
Fig.4
Fig.5

INTEGRATED DEVICE FOR REAL TIME QUANTITATIVE PCR

PRIOR RELATED APPLICATIONS

This application claims priority to Italian Application Number TO2012A000302, filed Apr. 5, 2012, and incorporated herein by reference in its entirety.

TECHNICAL FIELD

The present disclosure relates to an integrated device and method for real time quantitative PCR (Polymerase Chain Reaction).

BACKGROUND

Typical procedures for analyzing biological materials, such as nucleic acid, involve a variety of operations starting from raw material. These operations may include various degrees of cell purification, lysis, amplification or purification, and analysis of the resulting amplified or purified product.

As an example, in DNA-based blood tests the samples are often purified by filtration, centrifugation or by electrophoresis so as to eliminate all the non-nucleated cells. Then, the remaining white blood cells are lysed using chemical, thermal or biochemical means in order to liberate the DNA to be analyzed.

Next, the DNA is amplified by an amplification reaction. Beforehand, it is denatured by thermal, biochemical or chemical processes. The procedures are similar if RNA is to be analyzed, but more emphasis is placed on purification or other means to protect the labile RNA molecule. RNA is usually copied into DNA (cDNA) and then the analysis proceeds as described for DNA.

The discussion herein is simplified by focusing on detection of DNA by PCR amplification as an example of a biological molecule that can be analyzed using the present device. However, the present device and method can be used for other chemical or biological tests.

As indicated, PCR allows an initial amount of DNA strands, added to a reaction mix, to be multiplied. The amplification process includes basically three steps, including a denaturation step, where the DNA target, double-helix strands are separated into target single-helix strands by heating the mixture to a first high temperature, e.g. higher than 90° C.; an annealing step, where primers are annealed to the target single helix strands at a second, lower temperature, 50-65° C.; and an extension step, where new DNA strands, complementary to the DNA target strands, are synthesized at an intermediate temperature, e.g., at 70-85° C., forming double-helix amplification products, also called "amplicons".

Real time quantitative PCR is a widely used technique based on the real-time monitoring of PCR reaction during its progress, and can allow quantitation of initial target molecules based on amplification curves. This can be accomplished using fluorescent probes or dyes, such as ethidium bromide (EtBr), which intercalates into a double helix and then fluoresces. Thus, fluorescence increases when fluorescent probes or dyes bind with double-helix amplification products, and this increase in fluorescence can be monitored as the reaction proceeds and the level of amplification product exponentially increases. Labelled probes that hybridize to amplified sequences can be used in the same manner. The more initial target molecule present at the beginning of the reaction, the more signal will be obtained at a point t when the reaction is still in the exponential part of the amplification curve.

Although consolidated instruments are widely available on market, the current trend is to develop new devices aimed to increase throughput and portability. Such devices may involve packed arrays of nanoliter wells able to perform highly parallel screening of pre-charged cartridges for point-of-care applications.

Among the various aspects characterizing present real-time quantitative PCR (RTQ-PCR) instruments, such as reproducibility, parallelization, etc., one important aspect is related to the speed in executing tests. In fact, due to the inherent working methods of PCR, several cycles of amplification are necessary to detect product, each including switching the temperature between two or three different temperatures, as above discussed. Every cycle may take several seconds and tens of cycles are typically necessary to perform a test. In particular, when few initial DNA copies are available, the entire test can take one hour or more.

This can be a limiting aspect, in particular for point-of-care applications, where speed is a very important consideration.

This limitation may be clearly appreciated from the plots of FIGS. 1 and 2. FIG. 1 plots an RTQ-PCR curve showing the increasing fluorescence during cycling. As may be seen, the curve has three different portions; a starting one, portion A, where fluorescence remains low (background level); a second portion, portion B, after a point called Threshold Cycle "CT", where the curve grows exponentially for few cycles; and a final portion, portion C, where the curve saturates and no further amplification is seen.

In portion A, background fluorescence is dominant. Background fluorescence is intrinsic in RTQ-PCR methods and cannot be avoided, nor subjected to strong reduction simply by optimizing detection methods. In fact background fluorescence is due to the presence of free fluorescent probes or fluorophores in the reaction vessel or well. Due to the initial high concentration of the free fluorescent probes, in this initial portion fluorescence due to amplification is negligible or not distinguishable from the intrinsic fluorescence. After the threshold cycle CT, however, the fluorescence curve strongly increases due to the exponential growth of amplification products.

As shown in FIG. 2 (from sabiosciences.com/pathway7.php), the threshold cycle CT depends, i.a., on the concentration of the starting target strands in the reaction vessel (indicated laterally to each curve). As visible, in case of very low concentrations ($1\text{-}10^4$), the Threshold Cycle CT may require several amplification cycles; thus the entire procedure requires long time.

Thus, a need exists of providing a device and a method to reduce the time needed to perform RTQ-PCR.

Numerous techniques and methods have been proposed to improve the efficiency of RTQ-PCR.

EP2077336 discloses, e.g., a method for simultaneous quantitative analysis of multiple nucleic acid sequences in a single compartment, having the aim of increasing the number of different sequences that can be simultaneously detected. To this end, a number of surface-immobilized oligonucleotides probes, complementary to the multiple sequences to be detected, act as capture probes and are detected using a highly surface-specific readout device. Capture probes may be immobilized on paramagnetic beads attracted to a surface through a magnetic field.

US2008305481 discloses methods and systems that use fluorescently encoded superparamagnetic microspheres for the immobilization of amplification products during the PCR process. Also this document is directed to allowing multiplex analysis of RTQ-PCR.

Both known solutions are directed to increase multiplexing capability, by carrying out a single bead (or bead-by-bead) detection. Among various detection techniques, photodetection using Linear Lens Changer (LLC) or confocal detectors is taught. To discriminate against background fluorescence, the optical plane of the detector is set to be the surface where the beads are concentrated, thus improving the signal to noise ratio.

For allowing detection of beads immobilized on the bottom surface of the vessel, the use of either very complex detection techniques or of relatively large beads is required. In fact, confocal detectors are not able to discriminate fluorescence in volumes smaller than their resolution and have a minimum resolution of about 1 µm. In other words, they collect all the fluorescence emitted a volume that may be approximated by cylinder having a base diameter and a height of 1 µm.

This is not a problem for performing a bead-to-bead scanning, as suggested in a multiplexed detection, discussed in the above documents, since large beads may be used.

However, this solution does not solve the problem of substantially reducing the Threshold Cycle CT in the detection of a single type of amplification products, where discrimination between different target products is made using different vessels arranged in big arrays, if so desired.

In this case, in fact, the detection of a small amount of amplicons each time does not allow a reduction of the process time.

On the other hand, if beads of smaller dimensions are used, also a volume of the liquid overlying the layer of immobilized amplicons would be detected by the confocal reader, since the latter is not able to detect volumes smaller than its resolution. As a result, the free floating non-activated fluorophores would be detected as well. In such a case, the reading would be again affected by the background fluorescence.

The dependence of the thickness of layer immobilized on a surface of the vessel versus the bead dimensions and the obtainable gain are shown in FIGS. 3a, 3b, where FIG. 3b shows the right-hand portion of the curve of FIG. 3a, in an enlarged scale. Line D (whose values are shown on the left) plots the layer thickness as a function of the beads diameter, while line E plots the cycle gain (that is the reduction in the number of cycles necessary to reach the Threshold Cycle $C_T$ due to the reduction of dimensions in the beads). As is visible in the graph, the cycle gain increases considerably in case of smaller beads, but the simultaneous decrease of the thickness well below the confocal microscope resolution prevents the detection through a confocal detector. In other words, when a confocal detector is used, relatively big beads are be used, where the gain is low.

Thus, the aim of the disclosure resides in devising a method and a device overcoming the limitation of the known solutions and allowing a rapid RTQ-PCR in an array of vessels.

SUMMARY

According to the present disclosure, there are provided a method and a device for real-time quantitative detection of single target nucleic acid sequences, as defined in claims 1 and 9, respectively.

DESCRIPTION OF THE FIGURES

For the understanding of the present disclosure, preferred embodiments are now described, purely as a non-limitative example, with reference to the enclosed drawings, wherein:

FIG. 4 is a lateral view of a reaction microcell in a first step of the reaction;

FIG. 5 is a lateral view of the reaction microcell of FIG. 4 in a subsequent step of the reaction;

DETAILED DESCRIPTION

Figure 1:
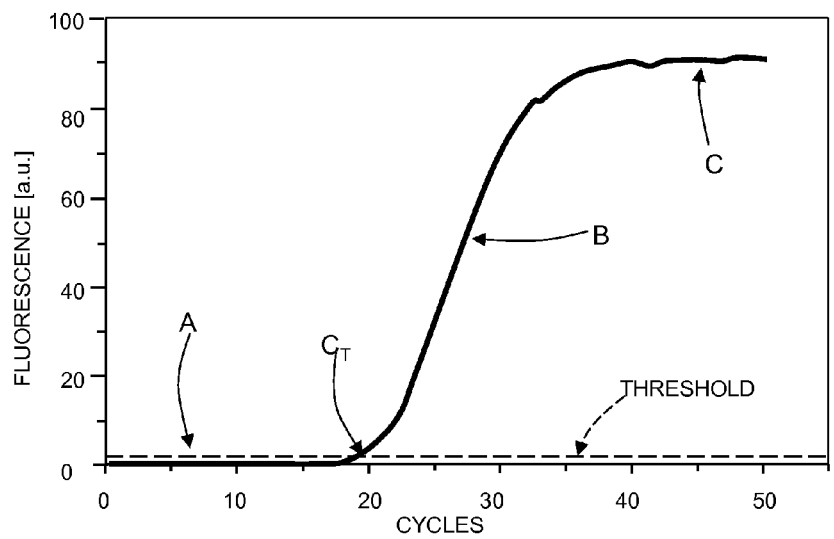
FIG. 1 shows the plot of the fluoresces vs. number of amplification cycles during a RTQ-PCR.
Figure 2:
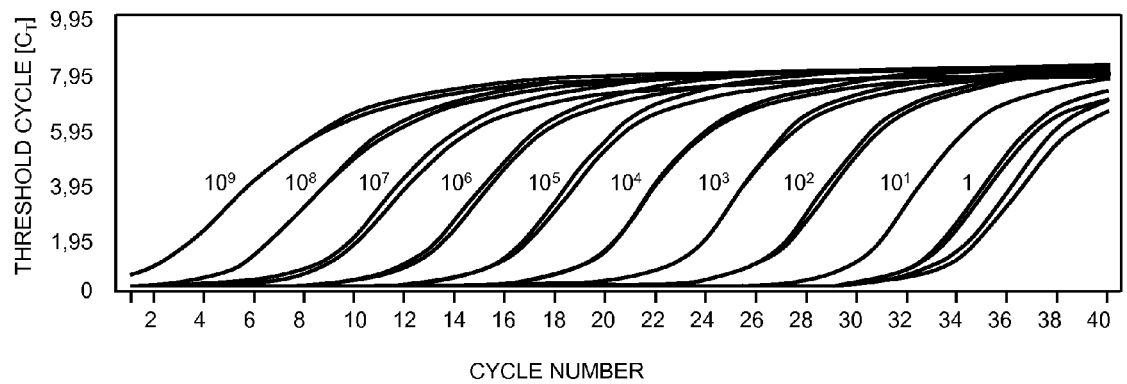
FIG. 2 shows the plots of the threshold cycles vs. the number of performed cycles as a function of the number of starting target sequences present in the sample.

According to one embodiment, paramagnetic or superparamagnetic nanobeads derivatized with primers are used. After each amplification cycle or after a number of amplification cycles, a magnetic field is applied to a well containing the reaction liquid to confine and concentrate the nanobeads into a multilayer formed by overlaying nanobeads, and fluorescence is read in the concentration layer using a surface-specific, spatially discriminating detection technique, e.g., using a confocal microscope.

In particular, the parameters of the method may be selected so that the multilayer has a thickness matched to the vertical resolution of the surface-specific reading device. Here, the term "matched" means the vertical resolution value±10%.

In addition, the parameters of the system may be selected so as to set the focal plane at a central region of the multilayer. Ideally, the focal plane is set at the median plane, that is at a height of h/2 with respect to the bottom wall, where h is the thickness of the multilayer, but also a distance in the range h/2±30% is acceptable.

Since fluorescence is measured in the nanobead confinement region formed by a multilayer having a thickness comparable with the reading vertical resolution, where the bonded probes are much more concentrated than non-bonded probes, the background fluorescence is strongly reduced, allowing the threshold cycle CT to be reached with fewer thermal cycles. Thus, RTQ-PCR measurements can be greatly speeded up.

Use of PCR primers linked to magnetic nanobeads has been already demonstrated in literature with the purpose of developing new assay methodology (see, e.g., Lermoa et al., "In situ DNA amplification with magnetic primers for the electrochemical detection of food pathogens", Biosensors and Bioelectronics 22(9-10): 2010-2017 (2007); see also C. S. Jacobsen, "Microscale detection of specific bacterial DNA in soil with a magnetic capture-hybridization and PCR amplification assay", Appl. Environ. Microbiol. 61(9): 3347-3352 (1995)).

Further, although we have exemplified the system using primers bound to magnetic beads, other assay formats may be possible. For example, magnetic nanoparticles or other magnetic labels, such as ferrocene-based labels, single molecule magnets, and the like, can be developed and used to magnetize the PCR products in other ways.

Since the nanobeads are magnetically confined in a multilayer having a preselectable thickness, beads having a diameter of a few nm may be used. For example, the nanobeads may have a diameter lower than 50 nm, preferably at most about 16 nm (e.g., less than 17 nm); more preferably between 5-10 nm, e.g., of about 5-6 nm, or even smaller (e.g., until 1-2 nm). Therefore, a very high concentration of the nanobeads in the multilayer is obtained, together with a very high compaction of activated fluorescent probes and the reduction of free space among the nanobeads. Consequently, also the number of non-activated fluorophores in the monitored region is also reduced to a negligible extent. Since all the activated fluorophores are contained in the detection region, their concentration increases, thus reducing the number of amplification cycles before Threshold Cycle CT is reached.

When nanobeads smaller than 17 nm are used, it has been demonstrated that they may be obtained as single crystals with superparamagnetic characteristics (see, e.g., Cafer T. Yavuz et al. "Low-Field Magnetic Separation of monodisperse nanocrystals, Science 314 (5801): 964-967 (2006), at page 966, left hand column, indicating a value of about 16 nm for iron oxide particles); to obtain nanobeads in the 17-50 nm range, it is necessary to include the single crystals in a matrix (e.g., polymeric), in a more complex and expensive way.

For furthering the compaction effect and reducing the effect of non-activated fluorophores, according to a further aspect, lateral confinement of the nanobeads is also proposed. To this end, each cell has its own magnet arranged below the bottom surface of a respective vessel and having a smaller diameter than the bottom surface of the well. Feasibility of obtaining containment of superparamagnetic material at low magnetic field has been demonstrated, e.g. in Cafer T. et al. (2006).

These and other aspects of the present system and method will be disclosed in detail hereinafter.

FIG. 4 shows a reaction microcell 1 for performing RTQ-PCR. Here the microcell 1 has a microwell 2 including lateral walls 3 and bottom wall 4. A magnet 5 extends in proximity of the bottom wall 4, here under the bottom wall 4, although the magnet could also be positioned in the bottom wall or over the bottom wall; in the latter case, a protective film (not shown) may cover the magnet 5 so that the materials do not interfere with the assay.

An objective 6, in particular a confocal objective, is arranged over the microwell 2 and is connected to a processing unit 8.

A power supply 7 is connected to the magnet 5 to activate it and generate a magnetic field in a detection step.

The microcell 1 is configured to perform RTQ-PCR and multi-layer fluorescence detection, as described hereinbelow.

In detail, initially a solution 10 is introduced in the microwell 2, for example by injection. The solution 10 comprises target double helix sequences (schematized at 11); magnetic primers 12 (that is, as shown in the enlarged detail, primers 13 immobilized on magnetic nanobeads 14); DNA polymerase (not shown), free fluorescent probes 15 and free dNTPs 16, in a per se known manner.

For example, the fluorescent probes 15 may be Sybr Green or other commercially available fluorescently labelled probes (e.g. molecular beacons, scorpions, lightup probes, etc.); the nanobeads 14 are of paramagnetic or superparamagnetic material such as nanocrystals of iron, magnetite ($Fe_3O_4$), maghemite ($\gamma Fe_2O_3$), so as to be easily magnetized in presence of a magnetic field and attracted by the magnet 5 to the bottom wall 4, but get back to the non-magnetized state, where they are free to move in the solution 10, as soon as the magnetic field is removed. As indicated, the nanobeads have a diameter smaller than 50 nm, preferably 5-10 nm, e.g. 5-6 nm.

Then, an amplification cycle is performed, in a per se known manner, including a denaturation step at a first, higher temperature, to obtain single strands from the target, double helix sequences; an annealing step, at a lower temperature, to allow annealing of the magnetic primers 12 to the single strands; and an extension step, at an intermediate temperature, where DNA polymerase syntheses new strands from the dNTPs 16, to obtain amplification products, shown schematically at 20 and including at some point fluorescent probes 15, as visible in the enlarged detail.

Then, the magnet 5 is energized, to generate a magnetic field, as schematically shown in FIG. 5. As indicated, the parameters of the magnetic field are selected so that the multilayer 22 has a thickness matched to the vertical resolution (also called "axial resolution" or "optical slice thickness") of the objective 6. For example, a magnetic field of about 1 Tesla is generated.

In addition, as discussed above, the system is designed so that the focal plane of the objective 6 is set at a central region of the multilayer 22. As a consequence, all the magnetic primers 12 are attracted toward the bottom wall 4 of the microwell 2. As above explained, due to the dimensions of the nanobeads 14, and the concentration thereof in the solution, all the nanobeads 12, either tied to respective amplicons or not yet bound, are attracted to the magnet and form a multilayer 22 of beads. During this step, the objective 6 reads the florescence in the multilayer 22 and generates a corresponding electrical signal S.

The electrical signal S generated by the objective 6 is sent to the processing unit 8, for standard processing.

As soon as the magnet 5 is deenergized, the nanobeads 14 are free to move away from the bottom wall 4 and, by virtue of the Brownian motion, are free to float away and to spread in the liquid 10 in the microwell 2.

The above cycle is repeated more times, until the fluorescence exceeds the threshold $C_T$ and the processing unit may generate the analysis results, usually providing the concentration of target molecules in the sample.

Figure 6:
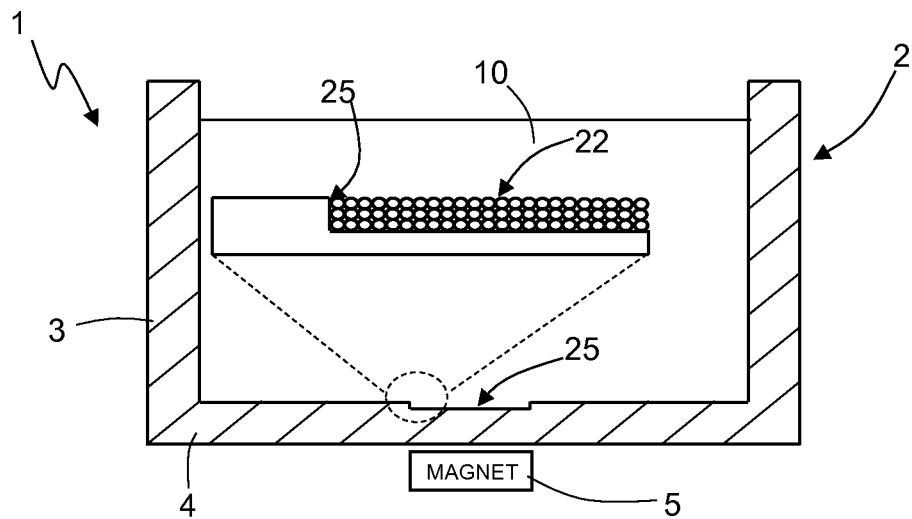
FIG. 6 is a lateral view of a different reaction microcell in the same step as FIG. 5.
Figure 7:
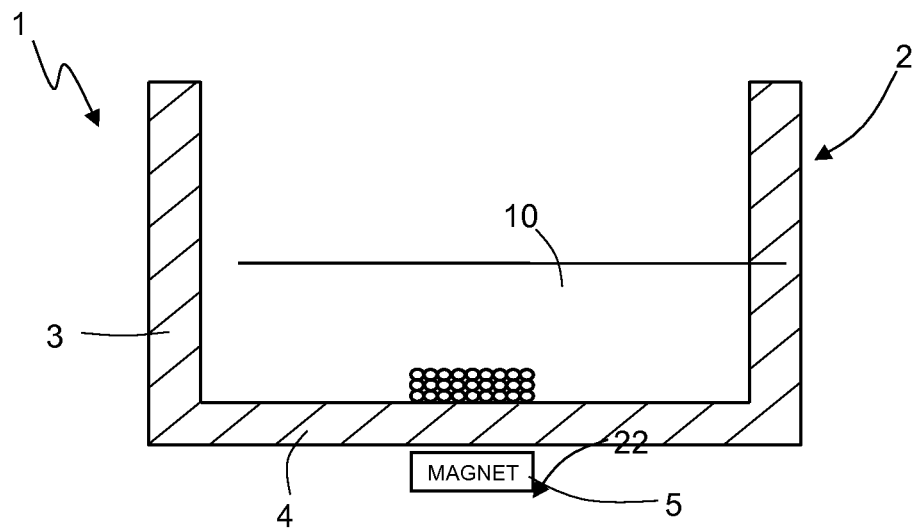
FIG. 7 shows another embodiment of the reaction microcell.

In the embodiments of FIGS. 6 and 7, lateral confinement is also performed. In detail, in both embodiments, the magnet 5 has a smaller diameter than the bottom wall 4, for example ⅕ to ¹⁄₁₀. By applying a sufficiently strong magnetic field, for example, of about 1 T, the nanobeads 14 feel a strong holding force that causes them to stack, to form a multilayer having a width about the same as the magnet dimension. This effect may be increased by providing a recess in the bottom wall 4, see e.g. FIG. 6 at 25, although this is not necessary (as shown in FIG. 7).

Figure 8:
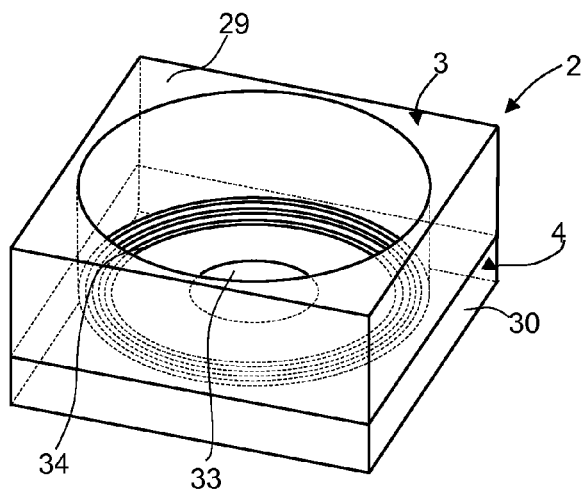
FIG. 8 is a prospective view of a microcell.
Figure 9:
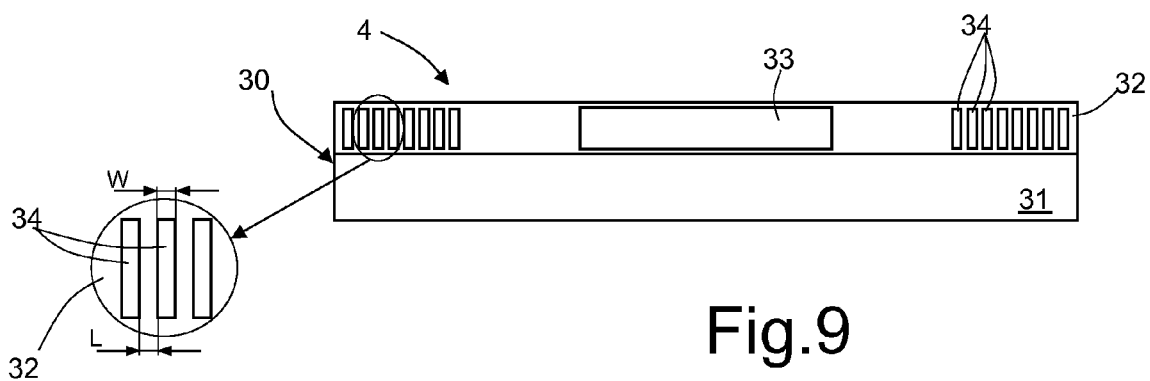
FIG. 9 shows a cross-section of a portion of the microcell of FIG. 8.

FIGS. 8 and 9 show another implementation of the microwell 2. Here, the lateral walls 3 are defined by a well body 29, of plastics, e.g. of polycarbonate, and are cylindrical. The bottom wall 4 is formed in a base body 30 different from the well body 29, and closes microwell 2 at the bottom. The base body 30 comprises a substrate 31 of semiconductor material, e.g. silicon, covered by a dielectric layer 32, e.g. of silicon dioxide.

A nucleus region 33, of ferromagnetic material such as iron, nickel, cobalt and alloys thereof, is embedded in the dielectric layer 32, in a central position of the base of the microwell 2. A coil 34 of conductive material, e.g. a metal such as aluminum, winds around the ferromagnetic region 33, at a distance therefrom, within the same dielectric layer 32. Coil 34 and nucleus region 33 form the magnet 5. Here, it is the width of the nucleus region 33 that determines the lateral confinement of the multilayer 22. In this manner, a microtiter plate having a magnetic base for each well can be made using standard and inexpensive semiconductor manufacturing techniques.

For example, the microcell 1 may have the following dimensions: diameter and height of the microwell 2: 300 μm; thickness of the nucleus region 33: 1-2 μm; thickness of the coil 34: 1-2 μm; thickness of the dielectric layer 32: slightly higher than the nucleus region and coil, just to cover them, e.g., 2-2.5 μm; inner radius of the coil 34: 250 μm; outer radius of the coil 34: 400 μm; width W of the aluminum strip forming the coil 34: 1.5 μm; distance L between the turns of the coil 34; number N of turns of the coil 34: 50; permeability Km of the nucleus region 33: 103. With such a microwell 2, by feeding the coil 34 with a current i of 10 mA, it is possible to generate a magnetic field BN of:

$$B_N = \sum_{n=1}^{N} \frac{\mu_0 i}{2R_n} K_m$$

$$B_N \sim 1T$$

wherein $\mu_o$ is vacuum permeability and $R_n$ is the radius of each turn of the coil 34, whose maximum value, in case, is limited by the magnetic saturation of the material of the nucleus region 33 (iron, nickel, cobalt and alloys).

Figure 10:
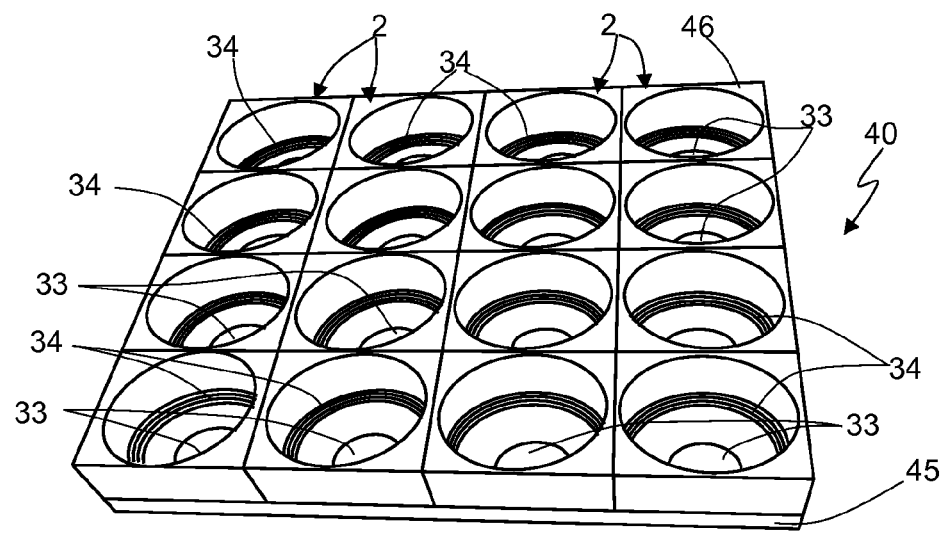
FIG. 10 is a prospective view of an array of microcells.

Microwell 2 may be part of a well array 40 having a common base body 45 (of semiconductor material, analogous to body 30 of FIG. 9) and a common wall body 46 (analogous to well body 29 of FIG. 9), as shown in FIG. 10, wherein the microwells 2 may be configured to detect a same target product or different microwells 2 may detect different targets.

Figure 11:
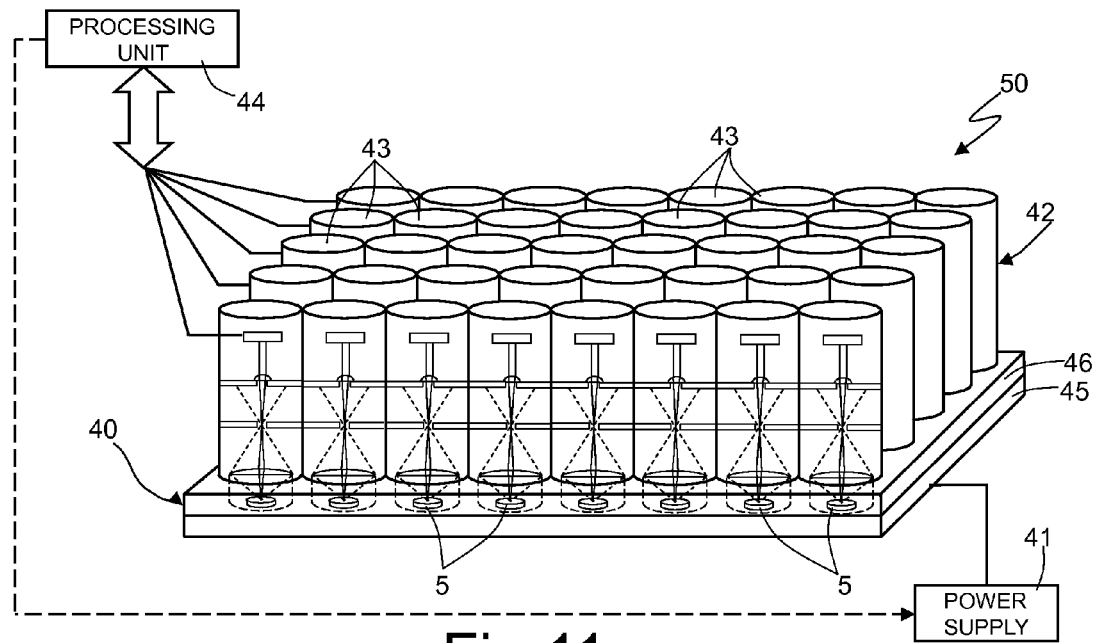
FIG. 11 shows an implementation of an integrated confocal detector element.

The well array 40 may be part of an integrated device for performing RTQ-PCR, as shown in FIG. 11. Here, the device 50 comprise the well array 40, a power source 41, common for all the microcells 2 and connected to the well array 40; a detector array 42, formed by a plurality of confocal optical detectors 43, arranged above the well array 40; and a processing unit 44, for controlling the various steps of the RTQ-PCR and the energization of the magnets 5. In case, the power supply 41 and the processing unit 44 may be integrated in the substrate 31 (not shown in 11) of the common base body 45 of semiconductor material.

The detector array 42 may be implemented by the confocal optical detector disclosed in Italian Patent application TO2011A000298, filed on 1 Apr. 2011 in the name of the same applicant, that is characterized by its small overall dimensions, and thus can be used in the system 50.

Figure 12:
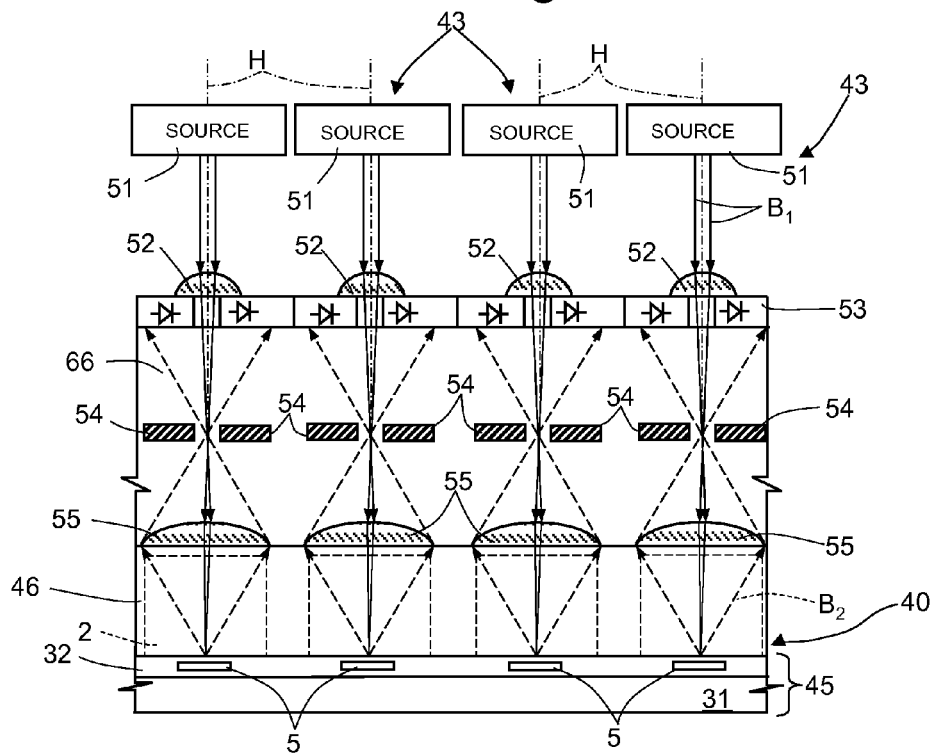
FIG. 12 shows a device for detection of RTQ-PCR including the microcells of FIG. 8 and the confocal detector elements of FIG. 11.

As shown in FIG. 12, each detector 43 comprises a light source 51), a first lens 52, an optoelectronic sensor 53, a pinhole 54, and a second lens 55, arranged in succession and vertically aligned.

Figure 3A:
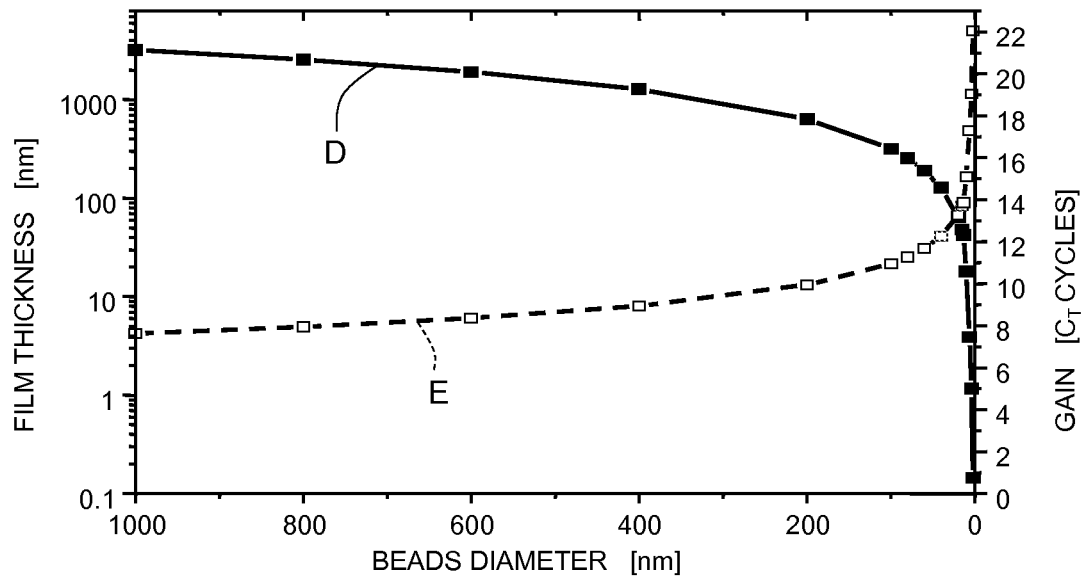
FIG. 3a shows the plot of the layer thickness and obtained gain vs. bead diameter.
Figure 3B:
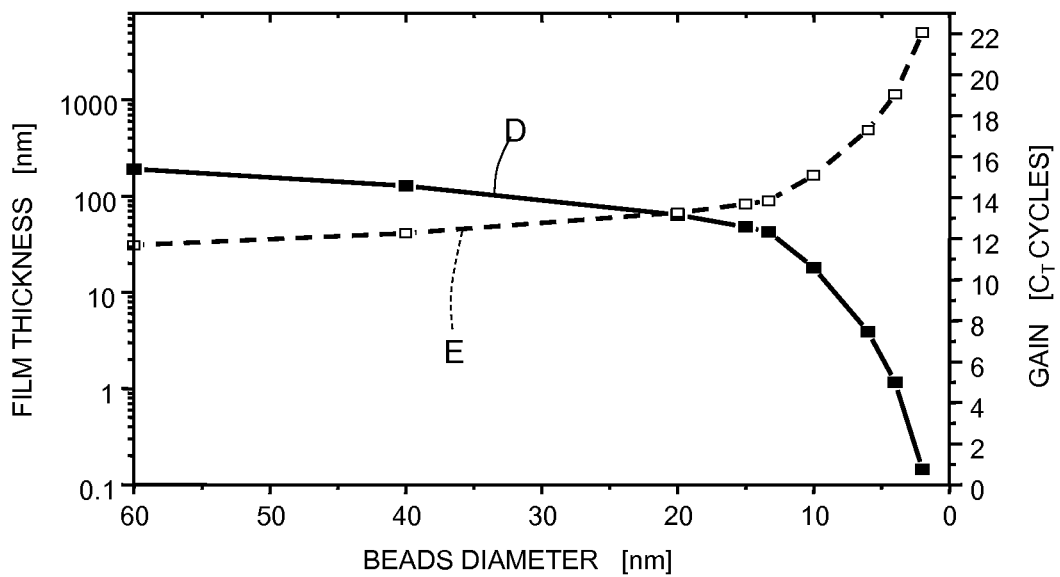
FIG. 3b shows a portion of the plot of FIG. 3a, in an enlarged scale.

Operatively, when the fluorescent probes 15 (FIG. 3) are illuminated by a first optical beam $B_1$ generated by the light source 51, they generate a second optical beam $B_2$ at a generally different wavelength.

Thus, the optical beams $B_1$ and $B_2$ propagate along detector axes H.

The optoelectronic sensor 53, the pinhole 54, and the second lens 55 may be formed within a same dielectric region 66, transparent for the used wavelengths, for example, silicon oxide $SiO_2$ to define a monolithic body. The second lens 55 may be of antimony trioxide $Sb_2O_3$ or $TiO_2$.

A simulation performed by the applicant shows the gain obtainable with the use of nanobeads arranged in a multilayer. In the simulation, a microwell 2 has been used having a radius and a height of 0.5 mm, thus a chamber volume of about 393 mL, a coil 34 with an outer diameter of 0.5 mm, a ferromagnetic region 33 with radius of 0.087 mm. The simulation was performed for beads of 10 nm setting a primer concentration of 100 nM and assuming a single primer for each nanobead 14; this sets a binding capacity of 3000 prime/$\mu m^2$ of bead surface. In case of 2D confinement (thus so as to have a multilayer 22 of 1 μm of thickness but no lateral confinement, for the same values, beads of 333 nm are used.

The simulation gave the results shown in Table I, wherein the concentration gain $G_C$ represents the gain of the ratio activated probes vs. non-activated probes in the confinement layer with respect to beads dispersed in the solution (no confinement). The high value of the concentration gain $G_C$ for the 3D-confinement demonstrates that only a very small fraction of the free probes are contained in the confinement layer 22. The table also shows the cycle gain $G_{CY}$ (that is the reduction of cycles to reach the Threshold cycles) obtainable with 3D- and 2D-confinement.

TABLE 1

SIMULATION RESULTS

|  | 3D confinement | 2D confinement |
| --- | --- | --- |
| Bead diameter | 10 nm | 330 nm |
| Layer thickness | 1 μm | 1 μm |
| Gain $G_C$ | 34868 | 986 |
| Gain $G_{CY}$ | 15.1 | 10.0 |

The advantages of the present method and device are clear from the above. In particular, it is emphasized that the described embodiments afford a very fast and sensitive RTQ-PCR, that is well reproducible, compatible with high throughput. The device may be manufactured with very small dimensions, depending mainly on the number of cells (vessels) in the array, each microwell 2 being able to perform a quick and reliable analysis with very small volumes of solutions, of a few nanoliters.

By virtue of the small dimensions, it is also possible to obtain rapid thermal ramps, thus further decreasing the analysis time; and the system may be manufactured using integrated circuit planar manufacturing technology, and thus shares its advantages of low cost, high reproducibility and reliability, small dimensions.

Finally, it is clear that numerous variations and modifications may be made to the described and illustrated herein, all falling within the scope of the invention as defined in the attached claims.

For example, the microwell 2 may have its own bottom wall and the magnet may be formed in a separate body, including the substrate 31 and the dielectric layer 32. The separate body or base may fit under the wells, thus bringing the magnetic coils into the desired position, beneath each well.

In addition, if the Threshold Cycle CT is known, the method may comprise performing a number of amplification cycles without fluorescence reading, and performing reading only when approaching the Threshold Cycle CT.

The following references are each incorporated herein in their entirety for all purposes:

Lermoa et al., "In situ DNA amplification with magnetic primers for the electrochemical detection of food pathogens", Biosensors and Bioelectronics 22(9-10): 2010-2017 (2007).

C. S. Jacobsen, "Microscale detection of specific bacterial DNA in soil with a magnetic capture-hybridization and PCR amplification assay", Appl. Environ. Microbiol. 61(9): 3347-3352 (1995).

Cafer T. Yavuz et al. "Low-Field Magnetic Separation of monodisperse nanocrystals, Science 314 (5801): 964-967 (2006).

EP2077336
US2008305481
US20120248347

The invention claimed is:

1. A method for real-time quantitative detection of a single target nucleic acid sequence, comprising:
   introducing into a microwell a sample comprising a target nucleic acid sequence, magnetic primers, and a labelled probe;
   performing one or more amplification cycles to form magnetic amplification products;
   attracting the magnetic primers to a surface through a magnetic field and forming a multilayer including the magnetic amplification products and the labelled probe hybridized thereto; and
   quantitatively detecting the magnetic amplification products by measuring the labelled probe in the multilayer with a spatially discriminating detection method during one or more of said amplification cycles using a spatially discriminating detection device having a vertical resolution, and the multilayer has a thickness matched to the vertical resolution of the spatially discriminating detection device.

2. The method according to claim 1, wherein detecting the magnetic amplification products and the labelled probe comprises using a spatially discriminating detection device having a focal plane and setting the focal plane at a central region of the multilayer.

3. The method according to claim 1, wherein introducing magnetic primers comprises using primers attached on paramagnetic beads having a diameter smaller than 50 nm.

4. The method according to claim 3, wherein the paramagnetic beads are single crystals.

5. The method according to claim 4, wherein the paramagnetic beads have a diameter of <17 nm.

6. The method according to claim 1, wherein attracting the magnetic primers comprises laterally confining the magnetic primers to obtain a multilayer of magnetic amplification products and the labelled probe having a smaller width than the surface.

7. The method according to claim 6, wherein attracting the magnetic primers comprises energizing a magnet extending laterally to the surface, said magnet having a smaller diameter or width than the diameter or width of the microwell.

8. A method for real-time quantitative detection of a single target nucleic acid sequence, comprising:
   introducing into a microwell a sample comprising a target nucleic acid sequence, magnetic primers, and a labelled probe;
   performing one or more amplification cycles to form magnetic amplification products;
   attracting the magnetic primers to a surface through a magnetic field and forming a multilayer including the magnetic amplification products and the labelled probe hybridized thereto; and
   quantitatively detecting the magnetic amplification products by measuring the labelled probe in the multilayer with a confocal detector or microscope during one or more of said amplification cycles.

9. The method according to claim 8, wherein the confocal detector or microscope has a focal plane and setting the focal plane at a central region of the multilayer.

10. The method according to claim 8, wherein introducing magnetic primers comprises using primers attached on paramagnetic beads having a diameter smaller than 50 nm.

11. The method according to claim 10, wherein the paramagnetic beads are single crystals.

12. The method according to claim 11, wherein the paramagnetic beads have a diameter of <17 nm.

13. The method according to claim 8, wherein attracting the magnetic primers comprises laterally confining the magnetic primers to obtain a multilayer of magnetic amplification products and the labelled probe having a smaller width than the surface.

14. The method according to claim 13, wherein attracting the magnetic primers comprises energizing a magnet extending laterally to the surface, said magnet having a smaller diameter or width than the diameter or width of the microwell.

* * * * *